United States Patent
Slade, Jr.

(10) Patent No.: US 8,375,896 B2
(45) Date of Patent: Feb. 19, 2013

(54) METHOD OF USE OF DICALCIUM PHOSPHATE AS AN ANTLER SCENT

(76) Inventor: Gaines B. Slade, Jr., Mobile, AL (US)

( * ) Notice: Subject to any disclaimer, the term of this patent is extended or adjusted under 35 U.S.C. 154(b) by 301 days.

(21) Appl. No.: 12/904,591

(22) Filed: Oct. 14, 2010

(65) Prior Publication Data

US 2012/0090557 A1 Apr. 19, 2012

(51) Int. Cl.
*A01K 15/02* (2006.01)
*A01K 29/00* (2006.01)

(52) U.S. Cl. ........................................ 119/712; 119/174
(58) Field of Classification Search .................. 119/712, 119/174, 839
See application file for complete search history.

(56) References Cited

U.S. PATENT DOCUMENTS

| | | | |
|---|---|---|---|
| 6,363,649 | B1 | 4/2002 | Lambert |
| 7,530,939 | B2 | 5/2009 | Forrester |
| 7,691,410 | B2 | 4/2010 | Fischer et al. |
| 2010/0144894 | A1 | 6/2010 | Fischer et al. |
| 2010/0189752 | A1* | 7/2010 | Kassouni et al. ............. 424/400 |
| 2011/0318448 | A1* | 12/2011 | Rudd et al. ........................ 426/1 |

OTHER PUBLICATIONS

MPR News, "Fetching fun: Teaching dogs to sniff out antlers", retreived Sep. 20, 2012, dated Mar. 15, 2010.*
DCA Newsletter Mar. 2006, "Training a Dog to Find Shed Antlers", by John Jeanneney, retreived Sep. 20, 2012, dated Mar. 23, 2008.*

* cited by examiner

*Primary Examiner* — Kimberly Berona
*Assistant Examiner* — Kathleen Iwasaki
(74) *Attorney, Agent, or Firm* — Kenneth M. Bush; Gerald M. Walsh; Bush Intellectual Property Law

(57) ABSTRACT

A method of producing the scent of deer antlers on a surface by forming an aqueous solution of dicalcium phosphate, and applying the aqueous solution to a surface so that the surface gives off a scent of deer antlers. The solution can be applied to the surface of an object and then a dog can be trained to locate the object, whereby the dog, after this training, will be able to locate shed antlers hidden in the environment; or the solution can be applied to a person or object whereby the application will mask the scent of the person and/or object with regard deer; or can be applied to any surface to attract deer to a desired location.

7 Claims, No Drawings

METHOD OF USE OF DICALCIUM PHOSPHATE AS AN ANTLER SCENT

FIELD OF THE INVENTION

The present invention relates to dicalcium phosphate and, more particularly, to the use of dicalcium phosphate in aqueous solution for application to surfaces to create an antler scent of all species of deer on the surfaces.

BACKGROUND OF THE INVENTION

Dicalcium phosphate, also known as calcium monohydrogen phosphate, is a dibasic calcium phosphate. It is usually found as the dihydrate, with the chemical formula of $CaHPO_4 \cdot 2H_2O$. It is practically insoluble in water, with a solubility of 0.02 g per 100 ml in water at 25° C. Dicalcium phosphate may be formed by the reaction of stoichiometric quantities of calcium oxide and phosphoric acid: $CaO + H_3PO_4 \rightarrow CaHPO_4 + H_2O$. Dicalcium phosphate is used as a dietary supplement in prepared breakfast cereals, dog treats, enriched flour, noodle products, and poultry feed. It is also used as a tableting agent in some pharmaceutical preparations, including some products meant to eliminate body odor. U.S. Pat. No. 7,530,939 discloses a method of reducing the leachability and odor of heavy metal bearing material or waste in incinerator bottom ash, comprising contacting the heavy metal bearing material or waste in the incinerator bottom ash with pulverized or fine particle dicalcium phosphate. U.S. patent Application Ser. No. 7,691,410 discloses a method to directly tablet or encapsulate pharmaceutical preparations with dicalcium phosphate powder.

While hunting remains a popular pastime, the popularity of collecting naturally shed big game antlers, such as those shed by whitetail deer, mule deer, elk, and other antlered species, is becoming increasingly popular. Shed antlers are a natural, renewable and recyclable big game "by-product." Once antlers are shed from their host, they are a natural by-product which deteriorates into the soil. Once collected, shed antlers are put to myriad uses. Antlers are used in the traditional medical practices of many cultures. They are used as decorative elements in lamps, furnishings, architecture, and other products. Hunters typically use shed antlers to "rattle in" game during hunting season. The demand for antlers is ever-increasing due to uses such as these. Looking for naturally shed antlers is much like hunting for a needle in a haystack Traditional methods of shed hunting involve scouting and tracking, but there is no predictable method that helps insure finding shed antlers. While the general season of antler shedding in a particular region may be known, it is impossible to predict the precise time and location at which a particular animal will shed its antlers. Tracking an animal such as a bull elk is a difficult and time-consuming task. To track such an animal for perhaps weeks at a time during shed season, hoping to be present at the precise moment of shedding, is impractical and generally not successful. A common approach is to provide feeders, or other attractants such as salt licks, for antlered game animals. Chicken wire is positioned in a generally funnel-shaped configuration in hopes of dislodging antlers about to be shed. Unfortunately, this practice has proven to have limited effectiveness. In addition, animals frequently are trapped in the chicken wire, wherein the animal can be badly injured or killed. There is a need for a simple, inexpensive, method for effectively and quickly locating shed antlers from antlered animals after they have been shed from the animal.

SUMMARY OF THE INVENTION

The present invention provides a method of using dicalcium phosphate as a deer antler scent by forming an aqueous solution of dicalcium phosphate and then applying the aqueous solution to a surface so the surface gives off a scent of antlers of several species of deer. Preferably, the aqueous solution of dicalcium phosphate is saturated with dicalcium phosphate. The aqueous solution of dicalcium phosphate may be applied to an object and a dog can be trained to locate the object because of the scent of the dicalcium phosphate on the object. The dog will then be able to readily locate shed antlers in the environment of any species of deer whose antlers give off the scent of dicalcium phosphate. The aqueous solution of dicalcium phosphate may be applied to an object or person to mask the scent of the object or person with regard to deer, or can be applied to any surface to attract deer of any species to any surface or desired location.

An advantage of the present invention is a method for rapidly locating shed antlers hidden in the environment.

Another advantage is an aqueous solution of dicalcium phosphate for simulating the scent of deer antlers which is inexpensive, easy to manufacture, and completely safe.

Another advantage is a scent to mask the scent of people and objects with regard to deer.

Another advantage is a scent to attract deer to a specific location.

DETAILED DESCRIPTION OF THE INVENTION

While the following description details the preferred embodiments of the present invention, it is to be understood that the invention is not limited in its application to the details of the steps of the method, since the invention is capable of other embodiments and of being practiced in various ways.

The inventor of the present invention has found that dogs can be trained with a shed antler to find shed antlers in the environment. However, since specific antlers may give off specific and various scents, using one shed antler from one species of deer limits this approach to finding shed antlers using a trained dog. It was surmised that a scent common to shed antlers of all deer species, and training a dog to that one scent, would greatly improve the use of a dog to find shed antlers hidden in the environment. It was unexpectedly discovered by the inventor that aqueous dicalcium phosphate provided a scent common to the antlers of whitetail deer, fallow deer, and the red stag. In view of the diversity of deer in which the antlers gave off a scent of dicalcium phosphate, it is reasonable to expect that all antlered deer will have antlers that give off this scent, further including mule deer, coues deer, sika deer, blacktail deer, elk, and moose.

The dicalcium phosphate used in the present invention is, preferably, put into water in excess of its solubility in water. Some of the dicalcium phosphate will dissolve in the water and some will precipitate. The resulting solution is filtered of any solids or precipitated dicalcium phosphate, thereby producing a saturated aqueous solution which provides or replicates a scent of deer antlers. As an example, 1 to 10 grams, preferably 5 grams of dicalcium phosphate are placed in 100 mls of water and stirred to allow a maximum amount of dicalcium phosphate to dissolve in the water. The water is then filtered to remove the dicalcium phosphate that did not dissolve. The saturated solution can be diluted with water to form solutions ranging in concentration from 1% of saturation up to 100% of saturation.

This aqueous solution of dicalcium phosphate can be placed on any suitable object at any desired effective concentration and a dog can be trained to find this object based upon the scent produced by this solution. The dog can then find shed antlers hidden in the environment of any species of deer, whose antlers give off the scent of dicalcium phosphate, by following this scent. The dog can be trained by standard methods known in the art for training dogs to identify and seek a specific scent, such as training a dog to follow the scent of a bird or the scent of chemicals such as drugs, narcotics, and explosive chemicals.

This aqueous solution of dicalcium phosphate can also be placed on people or objects in any desired effective concentration to mask the scent of people or the objects with regard to deer. For example, this aqueous solution of dicalcium phosphate can be placed on a person's clothing and hunting gear, and this dicalcium phosphate scent will mask the scent of people and other objects that give off scents that inform the deer of the presence of humans.

The dicalcium phosphate scent can also be used to attract deer to a specific location or object. This is accomplished by applying the aqueous solution of dicalcium phosphate in any desired effective concentration on, for example, mock scrapes on the ground or mock rubs on trees or to a deer decoy to mimic deer antler scent.

Instead of using an aqueous solution of dicalcium phosphate, dicalcium phosphate powder may be applied directly to surfaces. The dicalcium phosphate can be the sole ingredient in the powder. Alternatively, the dicalcium phosphate powder can be mixed with any suitable excipients or adhesives known in the art, such as, for example, a lubricant selected from the group consisting of magnesium stearate, calcium stearate, talc, solid polyethylene glycols, sodium lauryl sulfate or any other ingredient of similar nature alone or in a suitable combination thereof; a glidant selected from the group consisting of colloidal silicon dioxide or any other ingredient of similar nature alone or in a suitable combination thereof; a wetting agent selected from the group consisting of cetyl alcohol, glyceryl monostearate or any other ingredient of similar nature alone or in a suitable combination thereof; an absorbent selected from the group consisting of kaolin, bentonite clay or any other ingredient of similar nature alone or in a suitable combination thereof; a solution retarding agent selected from the group consisting of wax, paraffin or any other ingredient of similar nature alone or in a suitable combination thereof. In such a mixture, the dicalcium phosphate will form at least 1% by weight of the powder.

The foregoing description has been limited to specific embodiments of this invention. It will be apparent, however, that variations and modifications may be made by those skilled in the art to the disclosed embodiments of the invention, with the attainment of some or all of its advantages and without departing from the spirit and scope of the present invention. For example, the aqueous solution of dicalcium phosphate can be packaged in any suitable bottle, pressurized spray delivery container, pump spray container, or package containing moist wipes impregnated with the aqueous solution of dicalcium phosphate. The dicalcium phosphate may be used as the dihydrate or anhydrous form.

It will be understood that various changes in the details, materials, and arrangements of the parts which have been described and illustrated above in order to explain the nature of this invention may be made by those skilled in the art without departing from the principle and scope of the invention as recited in the following claims.

The invention claimed is:

1. A method of training a dog to locate shed antlers, comprising:
    a) Providing dicalcium phosphate for simulating a scent of deer antlers;
    b) Applying the dicalcium phosphate to an object so that the object gives off a scent associated with shed deer antlers;
    c) Using said object to scent train a dog to locate the object and shed deer antlers having a scent associated with the object; and
    d) Placing the dog in an environment of any deer species to locate shed antlers.

2. The method of claim 1, wherein the dicalcium phosphate is provided in an aqueous solution.

3. The method of claim 2, wherein said aqueous solution is a saturated solution of dicalcium phosphate.

4. The method of claim 3, wherein said saturated solution is diluted with water to form a diluted solution having a dicalcium phosphate concentration ranging from 1% of saturation up to 100% saturation.

5. The method of claim 1, wherein said dicalcium phosphate is provided as a powder.

6. The method of claim 5, wherein said dicalcium phosphate is the sole ingredient in said powder.

7. The method of claim 5, wherein said powder is mixed with any suitable excipients or adhesives.

* * * * *